US008980584B2

(12) United States Patent
Williams

(10) Patent No.: US 8,980,584 B2
(45) Date of Patent: *Mar. 17, 2015

(54) SYSTEM AND METHODS FOR NUCLEIC ACID SEQUENCING OF SINGLE MOLECULES BY POLYMERASE SYNTHESIS

(75) Inventor: John G. K. Williams, Lincoln, NE (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 341 days.

This patent is subject to a terminal disclaimer.

(21) Appl. No.: 11/923,597

(22) Filed: Oct. 24, 2007

(65) Prior Publication Data
US 2010/0093068 A1 Apr. 15, 2010

Related U.S. Application Data

(60) Continuation of application No. 11/757,289, filed on Jun. 1, 2007, which is a continuation of application No. 10/438,639, filed on May 14, 2003, now Pat. No. 7,229,799, which is a division of application No. 09/859,104, filed on May 14, 2001, now Pat. No. 6,762,048, which is a division of application No. 09/460,303, filed on Dec. 13, 1999, now Pat. No. 6,255,083.

(60) Provisional application No. 60/115,496, filed on Jan. 11, 1999, provisional application No. 60/112,078, filed on Dec. 14, 1998.

(51) Int. Cl.
| C12P 19/34 | (2006.01) |
| C12Q 1/68 | (2006.01) |
| C07H 21/02 | (2006.01) |
| C07H 21/04 | (2006.01) |
| C07H 21/00 | (2006.01) |
| C07H 19/10 | (2006.01) |
| C07D 209/12 | (2006.01) |
| C07H 19/20 | (2006.01) |

(52) U.S. Cl.
CPC .............. *C07H 19/10* (2013.01); *C07D 209/12* (2013.01); *C07H 19/20* (2013.01); *C07H 21/00* (2013.01); *C12Q 1/6869* (2013.01)
USPC ......... 435/91.2; 435/6.1; 435/6.11; 435/6.12; 435/91.1; 536/23.1; 536/24.3; 536/24.33; 536/25.3

(58) Field of Classification Search
USPC ............. 435/6, 91.1, 91.2, 183, 283.1, 287.1, 435/287.2, 6.1, 6.11, 6.12; 436/94, 501; 536/23.1, 24.3, 24.33, 25.3; 422/50, 422/68.1
See application file for complete search history.

(56) References Cited

U.S. PATENT DOCUMENTS

| 4,793,705 A | 12/1988 | Shera |
| 4,863,849 A | 9/1989 | Melamede |
| 4,962,037 A | 10/1990 | Jett et al. |
| 4,979,824 A | 12/1990 | Mathies et al. |
| 4,996,143 A | 2/1991 | Heller et al. |
| 5,302,509 A | 4/1994 | Cheeseman |
| 5,397,698 A | 3/1995 | Goodman et al. |
| 5,405,746 A | 4/1995 | Uhlen |
| 5,405,747 A | 4/1995 | Jett et al. |
| 5,489,508 A | 2/1996 | West et al. |
| 5,518,900 A | 5/1996 | Nikiforov et al. |
| 5,534,424 A | 7/1996 | Uhlen et al. |
| 5,547,839 A | 8/1996 | Dower et al. |
| 5,552,270 A | 9/1996 | Khrapko et al. |
| 5,597,910 A | 1/1997 | Gudibande et al. |
| 5,599,675 A | 2/1997 | Brenner |
| 5,608,063 A | 3/1997 | Hobbs, Jr. et al. |
| 5,661,028 A * | 8/1997 | Foote .......................... 435/287.2 |
| 5,674,743 A | 10/1997 | Ulmer |
| 5,714,330 A | 2/1998 | Brenner et al. |
| 5,736,318 A | 4/1998 | Munger et al. |
| 5,843,767 A * | 12/1998 | Beattie ........................ 435/287.1 |
| 5,849,478 A | 12/1998 | Cashman |
| 5,858,671 A | 1/1999 | Jones |
| 5,863,502 A | 1/1999 | Southgate et al. |
| 5,942,397 A | 8/1999 | Tarlov et al. |
| 5,952,174 A | 9/1999 | Nikiforov et al. |
| 6,099,823 A | 8/2000 | Falb |
| 6,136,543 A | 10/2000 | Anazawa et al. |
| 6,210,896 B1 | 4/2001 | Chan |
| 6,232,075 B1 | 5/2001 | Williams |
| 6,255,083 B1 | 7/2001 | Williams |
| 6,270,965 B1 * | 8/2001 | Kleiber et al. ............... 435/6.11 |
| 6,287,821 B1 | 9/2001 | Shi et al. |
| 6,306,607 B2 | 10/2001 | Williams |
| 6,355,420 B1 | 3/2002 | Chan |

(Continued)

FOREIGN PATENT DOCUMENTS

| WO | WO 89/09283 | 10/1989 |
| WO | WO 90/01069 A1 | 2/1990 |

(Continued)

OTHER PUBLICATIONS

Castro, et al., *Anal. Chem.*, 69:3915-3920 (1997).
Chen, et al., *Anal. Chem.*, 68:690-696 (1996).
Davis, et al., *Gata* 8(1):1-7, (1991).
Eigen, et al., *Proc. Natl. Acad. Sci. USA*, 91:5740-5747 (1994).
European Search Report 99967297.5-2402-US992985; Jan. 3, 2003.
Funatsu, et al., *Nature*, 374:555-559 (1995).
Harju, L., et al., "Colorimetric Solid-Phase Minisequencing Assay Illustrated by Detection of $\alpha_1$-Antitrypsin Z Mutation," *Clin Chem.* 39(11):2282-2287 (1993).
Hirschfeld, *Applied Optics* 15:12:2965-2966 (1976).

(Continued)

*Primary Examiner* — Frank Lu
(74) *Attorney, Agent, or Firm* — Kilpatrick Townsend & Stockton LLP

(57) ABSTRACT

This invention relates to improved methods for sequencing and genotyping nucleic acid in a single molecule configuration. The method involves single molecule detection of fluorescent labeled PPi moieties released from NTPs as a polymerase extension product is created.

14 Claims, 7 Drawing Sheets

(56) References Cited

U.S. PATENT DOCUMENTS

| | | | |
|---|---|---|---|
| 6,376,181 B2* | 4/2002 | Ramsey et al. | 435/6 |
| 6,403,311 B1 | 6/2002 | Chan | |
| 6,436,355 B1 | 8/2002 | Lee et al. | |
| 6,482,938 B1 | 11/2002 | Hayashizaki et al. | |
| 6,762,048 B2* | 7/2004 | Williams | 435/287.1 |
| 6,780,591 B2 | 8/2004 | Williams et al. | |
| 6,787,308 B2 | 9/2004 | Balasubramanian et al. | |
| 6,869,764 B2 | 3/2005 | Williams et al. | |
| 7,037,687 B2 | 5/2006 | Williams et al. | |
| 7,056,666 B2 | 6/2006 | Dower et al. | |
| 7,169,560 B2 | 1/2007 | Lapidus et al. | |
| 7,229,799 B2 | 6/2007 | Williams | |
| 7,329,492 B2 | 2/2008 | Hardin et al. | |
| 7,645,596 B2 | 1/2010 | Williams et al. | |
| 7,745,116 B2 | 6/2010 | Williams | |
| 7,767,400 B2 | 8/2010 | Harris | |
| 2003/0186227 A1* | 10/2003 | Balasubramanian et al. | 435/6 |

FOREIGN PATENT DOCUMENTS

| | | |
|---|---|---|
| WO | WO 90/13666 | 11/1990 |
| WO | WO 91/06687 A1 | 5/1991 |
| WO | WO 93/23564 | 11/1993 |
| WO | WO 96/27025 | 9/1996 |
| WO | WO 96/35779 | 11/1996 |
| WO | WO 98/13523 | 4/1998 |
| WO | WO 98/28440 | 7/1998 |
| WO | WO 98/44152 A1 | 10/1998 |
| WO | WO 99/05315 | 2/1999 |

OTHER PUBLICATIONS

Ihalainen, J., et al., "Towards Automatic Detection of Point Mutations: Use of Scintillating Microplates in Solid-Phase Minisequencing," *BioTechniques* 16(5)938-943 (1994).
Ishikawa, et al., *Jpn. J. Appl. Phys.*, 33:1571-1576 (1994).
Lee, et al., *Anal. Chem.*, 66:4142-4149 (1994).
Metzker, M., et al., *Nucleic Acids Research*, 22(20):4259-4287 (1994).
Moerner, *Science*, 277:1059-1060 (1997).
Nie, et al., *Science*, 266:1018-1021 (1994).
Nie, et al., *Annu. Rev. Biophys. Biomol. Struct.*, 26:567-96 (1997).
Nie, et al., *Anal. Chem.*, 67:2849-2857 (1995).
Nyrén, et al., "Solid Phase DNA Minisequencing by an Enzymatic Luminometric Inorganic Pyrophosphate Detection Assay", *Analytical Biochemistry*, 208:171-175 (1993).
Plakhotnik, T., et al., *Annu. Rev. Phys. Chem.*, 48:181-212 (1997).
Ronaghi, et al., *Science*, 281:363-365 (1998).
Sato, et al., *J. Chem. Research* (S):390-391 (1994).
Sauer, M., et al., *Chemical Physics Letters*, 254:223-228 (1996).
Schmidt, et al., *Proc. Natl. Acad. Sci. USA*, 93:2926-2929 (1996).
Tokunaga, et al., *Biochemical and Biophysical Research Communications*, 235:47-53 (1997).
Vale, R., et al., *Nature*, 380:451-453 (1996).
Yarbrough, et al., *The Journal of Biological Chemistry*, 254(23):12069-12073 (1979).
Yarbrough; Stacking Interactions in Fluorescent Nucleotide Analogs Containing 1-Aminophthalene-5-sulfonate at the Phosphoryl Terminus; *Journal of Biological Chemistry*; 1980: pp. 9907-9911; vol. 255, No. 20; U.S.A.
Zhu, et al., *Cytometry*, 28:206-211 (1997).
Schlageck; Spectroscopic Techniques for Study of Phosphodiester Bond Formation by *Escherichia coli* RNA Polymerase; *Journal of Biological Chemistry*; 1979; pp. 12074-12077; vol. 254, No. 23; U.S.A.
Communication of a notice of opposition from the European Patent Office dated Dec. 27, 2006 in Application No. 99967297.5.
Ambrose et al.; Alterations of Single Molecule Fluorescence Lifetimes in Near-Field Optical Microscopy; Science, vol. 265; Jul. 1994.
Goodwin et al.; Application of Single Molecule Detection to DNA Sequencing; Nucleosides & Nucleotides, 16(5&6), 543-550; 1997.
Ha, et al.; Single molecule fluorescence spectroscopy of enzyme conformational dynamics and cleavage mechanism; Proc. Natl. Acad. Sci. USA; vol. 96; previously presented 893-898; Feb. 1999.
Keller et al.; Single Molecule Fluorescence Analysis in Solution; Applied Spectroscopy, vol. 50, No. 7, 1996.
Orrit, et al.; Single molecule fluorescence: from excitation spectra to time correlation; Jour. of Luminescence 60&61, previously presented 991-996; 1994.
Tyagi; Proximity between Nucleotide/Dinucleotide and Metal Ion Binding Sites in DNA-Dependent RNA Polymerase from *Escherichia coli*; Biochemistry; vol. 31; previously presented 6447-6453; 1992.
Weiss; Fluorescence Spectroscopy of Single Biomolecules; Science; vol. 283, previously presented 1676-1683; 1999.
Wu, et al.; Fluorescence Resonance Energy Transfer Studies on the Proximity Relationship between the Intrinsic Metal Ion and Substrate Binding Sites of *Escherichia coli* RNA Polymerase; Jour. of Biological Chemistry; vol. 262, No. 27; pp. 13147-13154; 1987.
U.S. Appl. No. 95/001,529, filed Jan. 27, 2011.
U.S. Appl. No. 95/001,530, filed Jan. 27, 2011.
U.S. Appl. No. 95/001,531, filed Jan. 27, 2011.
U.S. Appl. No. 95/001,532, filed Jan. 27, 2011.
"Declaration" Interference No. 105677, *John G.K. Williams (Junior Party) Application No. 11/459,182 v. Susan Hardin et al. (Senior Party) Patent No. 7,329,492*, filed Dec. 18, 2008, 7 pages.

* cited by examiner

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:CFTR gene

```
            PCR primer 1

<400> SEQUENCE: 1
caccattaaa gaaaatatca t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:CFTR gene
      PCR primer 2
<220> FEATURE:
<221> NAME/KEY: modified_base
<222> LOCATION: (1)
<223> OTHER INFORMATION: n = biotinyl-cytosine

<400> SEQUENCE: 2
ntgtatctat attcatcata g                                              21

<210> SEQ ID NO 3
<211> LENGTH: 54
<212> TYPE: DNA
<213> ORGANISM: Artificial Sequence
<220> FEATURE:
<223> OTHER INFORMATION: Description of Combined DNA/RNA Molecule:CFTR
      gene normal allele
<220> FEATURE:
<223> OTHER INFORMATION: Description of Artificial Sequence:CFTR gene
      normal allele

<400> SEQUENCE: 3
caccattaaa gaaaatatca tcuuuggugu uuccuaugau gaauauagau acag          54

<210> SEQ ID NO 4
<211> LENGTH: 51
<212> TYPE: DNA
<213> ORGANISM: Artificial Sequence
<220> FEATURE:
<223> OTHER INFORMATION: Description of Combined DNA/RNA Molecule:CFTR
      gene deletion mutant allele
<220> FEATURE:
<223> OTHER INFORMATION: Description of Artificial Sequence:CFTR gene
      deletion mutant allele

<400> SEQUENCE: 4
caccattaaa gaaaatatca tugguguuuc cuaugaugaa uauagauaca g             51
```

SYSTEM AND METHODS FOR NUCLEIC ACID SEQUENCING OF SINGLE MOLECULES BY POLYMERASE SYNTHESIS

CROSS-REFERENCE TO RELATED APPLICATIONS

This application claims priority to U.S. Provisional Patent Application Ser. Nos. 60/112,078, filed Dec. 14, 1998, and 60/115,496, filed Jan. 11, 1999, the disclosures of which are hereby incorporated by reference in their entirely for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention relates to improved methods for sequencing and genotyping nucleic acid in a single molecule configuration. The method involves single molecule detection of fluorescent labeled pyrophosphate [PPi] moieties released from nucleotide triphosphate [NTPs] as a polymerase extension product is created.

BACKGROUND OF THE INVENTION

Previous non-electrophoretic sequencing and genotyping methods have not taken advantage of the continuous detection of PPi release from incorporated nucleotides. In the prior art of PPi sequencing (www.pyrosequencing.com), each nucleotide Adenosine-5' phosphate "A", Cytidine 5'-phosphate "C", Guanosine 5'-phosphate, Uridine 5'-phosphate "U" and Thymidine 5'-phosphate "T", is added separately to a reaction mixture containing the nucleic acid target and a polymerase. The current nucleotide is removed before the next is added. Incorporation of a nucleotide is accompanied by release of PPi from the NTP, detected by a secondary assay for PPi. A secondary assay is required because the PPi moiety of the NTP is not labeled. Only one nucleotide can be tested per cycle; if all 4 NTPs were present simultaneously, the polymerization reaction would continue uncontrolled and no sequence information could be obtained. Read length is limited by loss of synchronization among the target nucleic acid molecules in the sample.

Other non-electrophoretic methods, such as the stepwise ligation and cleavage of probes on DNA fragments attached to microbeads, requires synchronization of the DNA molecules that inevitably decays with each cycle.

The present method solves these problems and has advantages over other sequencing methods. Stepwise addition of nucleotides is unnecessary, as all four nucleotides are added simultaneously. Sequence information is produced continuously as polymerases continually incorporate all four nucleotides into growing nucleic acid [NA] chains. There is no loss of synchronization because single molecules are observed separately. Analysis of single molecules also allows for the use of NA fragments taken directly from organisms. With the present method, it is no longer necessary to prepare NA for sequencing using cloning or amplification processes, although NA so prepared can still be sequenced. In addition, there is the possibility of sequencing and genotyping many different nucleic acids on a single surface simultaneously.

SUMMARY OF THE INVENTION

Figure 1:
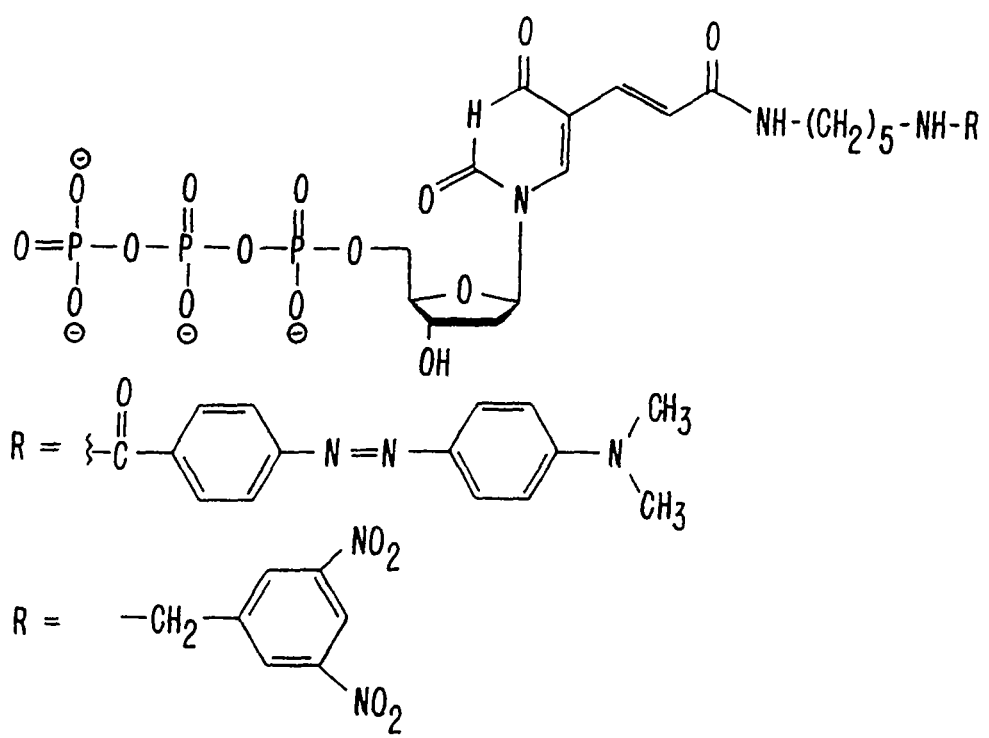
FIG. 1 is the chemical structure of quenching moieties connected through a linker to uracil.

This invention provides for a method of genotyping or sequencing a target nucleic acid [NA] comprising the steps of: i. immobilizing a nucleic acid polymerase or the target nucleic acid onto a solid support in a single molecule configuration; ii. contacting the solid support with a solution containing: (a) a target nucleic acid where the polymerase is immobilized or a polymerase where the target nucleic acid is immobilized; (b) a primer nucleic acid which complements a region of the target nucleic acid downstream of the region to be sequenced; (c) NTP where each type of base is differently labeled on the phosphate portion, where the labels provide a unique signal that is selectively detectable upon incorporation of NTP into the polymerase extension product; iii. permitting the polymerase to sequentially extend the primer incorporating the NTP creating a complement to the target nucleic acid; and, iv. determining extension of the primer by detecting the unique signal from the labeled NTP to genotype or to sequence the target nucleic acid. The method may use a solution which contains at least two different types of NTP.

It is preferred that the NTPs are labeled on the gamma phosphate with a fluorescent label that differentially fluoresces when the gamma phosphate is cleaved away from the nucleoside. The immobilized moieties can further comprise an array of locations each bearing a single molecule of polymerase or target nucleic acid. The immobilized moiety can be a polymerase positioned as an array of individual, single molecules onto a solid support. For genotyping the target nucleic acid may be a single nucleotide polymorphism. In such circumstances one need only add a solution which has a single type of NTP. For sequencing the detection involves a sequential detection of different types of NTP to provide the sequence of the target nucleic acid. In a preferred embodiment, the dNTP is labeled with a fluorophore on the gamma phosphate and a quencher moiety. In another preferred embodiment the solution contacting the solid support flows past the immobilized polymerase or target NA. The polymerases can be DNA dependent or RNA dependent DNA polymerases or DNA dependent RNA polymerases. The NTPs can be ribonucleotide triphosphates [rNTPs] or deoxynucleotide triphosphates [dNTPs] depending on the target nucleic acid and the polymerase in use.

This invention further includes a system for genotyping or sequencing a target NA comprising: i. a solid support having a surface bearing an immobilized nucleic acid polymerase or the target NA in a single molecule configuration; ii. a solution for contacting the surface containing: (a) a target NA where the polymerase is immobilized or a polymerase where the target NA is immobilized; (b) where the polymerase requires the use of a primer nucleic acid there is added a primer which complements a region of the target NA downstream of the region to be sequenced; (c) a molar excess of NTP, where each type of NTP base is differently labeled on the phosphate portion and where the labels provide a unique signal that is selectively detectable upon incorporation of the NTP into the polymerase extension product. The system embraces the same embodiments identified above for the methods. Where the system involves flowing solutions, the force for the flow may be mechanically generated or electroosmotically generated using electrodes.

This invention further provides for a solid support having a surface where the surface has a nucleic acid polymerase array attached to it wherein the members of the array consist of individual molecules of polymerase. The array members are optionally addressed so that the locations are defined and comparative information between sites can be generated and recorded by the optical reader. The solid support may have DNA dependent DNA polymerase or a DNA dependent RNA polymerase or a RNA dependent DNA polymerase (reverse transcriptase) attached to it. Preferably the immobilized moieties are in a single molecule configuration.

DEFINITIONS

"Addressable" in the context of an array refers to members of the array located in discrete and defined regions.

"Array" refers to a solid support having more than one site or location having either a target nucleic acid or a nucleic acid polymerase bound thereto.

"Complements a region of the target nucleic acid downstream of the region to be sequenced" in the context of sequencing or genotyping refers to the fact that the primers are extended in a 3' direction by a polymerase. Therefore the primer binds to a subsequence of the target 3' (downstream) to the target sequence that is to be determined as the 3' end of the primer is extended.

"Genotyping" is a determination of allelic content of a target DNA without necessarily determining the sequence content of the entire DNA. It is a subset of sequencing. For example the identification of single nucleotide polymorphisms by determination of single base differences between two known forms of an allele is a form of sequencing that does not require all the target DNA to be sequenced.

"Immobilizing" refers to the attachment of a target nucleic acid or polymerase to a solid support by a means that prevents its release in a reaction solution. The means can be covalent bonding or ionic bonding or hydrophobic bonding.

"Optical reader" refers to a device that can detect and record light emitted from the labeled dNTP.

"Sequencing" refers to the determination of the order and position of bases in a Nucleic acid.

"Single molecule configuration" refers to an array of molecules on a solid support where members of the array are present as an individual molecule located in a defined location. The members can be the same or different.

"Type of base" in the context of nucleotide triphosphates [NTPs] refers to nucleotides able to be recognized as a substrate for the polymerase. Typical bases include adenine, cytosine, guanine, uracil, or thymine bases where the type refers to the subpopulation of nucleotides having that base within a population of NTPs bearing different bases. Other rarer bases or analogs can be substituted such as xanthine or hypoxanthine or methylated cytosine.

DETAILED DESCRIPTION

1. Introduction

This invention provides for a novel means to genotype and sequence a nucleic acid. The method described herein uses individual fluorogenic NTP molecules that are identified one at a time as a RNA or DNA dependent polymerase incorporates their respective NTP into the extension products. The NTPs carry two adducts: a fluorescent dye attached to the gamma phosphate and a fluorescence quencher attached to either the base or sugar or dye. When the quencher is attached to the base or sugar, the NTP is hydrolyzed upon incorporation into the extension product and the liberated pyrophosphate-dye moiety becomes fluorescent. The free dye now unquenched, becomes fluorescent and its appearance is imaged at video-rate under a microscope.

A flowing stream sweeps the dye away from the parent molecule. All four NIPS are present simultaneously. As the polymerase continues to move along the target nucleic acid, the nucleotide sequence is read from the order of the released dyes.

2. Sources of Target Nucleic Acid

The target nucleic acid is not critical and can come from a variety of standard sources. It can be mRNA, ribosomal RNA, genomic DNA or cDNA. When the target is from a biological source, there are a variety of known procedures for extracting nucleic acid and optionally amplified to a concentration convenient for genotyping or sequence work. Nucleic acid can be obtained from any living cell of a person, animal or plant. Humans, pathogenic microbes and viruses are particularly interesting sources.

Nucleic acid amplification methods are also known. Preferably, the amplification is carried out by polymerase chain reaction (PCR) (U.S. Pat. Nos. 4,683,202. 4,683,195 and 4,889,818; Gyllenstein et al., 1988, Proc. Natl. Acad. Sci. USA 85: 7652-7656; Ochman et al., 1988, Genetics 120: 621-623; Loh et al., 1989, Science 243: 217-220; Innis et al., 1990, PCR Protocols, Academic Press, Inc., San Diego, Calif.). Other amplification methods known in the art can be used, including but not limited to ligase chain reaction (see EP 320,308) use of Q-beta replicase, or methods listed in Kricka et al., 1995, Molecular Probing, Blotting, and Sequencing, Chap. 1 and Table IX, Academic Press, New York.

3. Immobilization

The single molecule arrays of use in this invention involve a support, a bioreactive or bioadhesive layer and a bioresistant layer. The support can be glass, silica, plastic or any other conventionally non-reactive material that will not create significant noise or background for the fluorescent detection methods. The bioadhesive layer can be an ionic adsorbent material such as gold, nickel, or copper (Montemagno and Bachand (1999) Constructing nanomechanical devices powered by biomolecular motors. Nanotechnology 10: 225-231), protein-adsorbing plastics such as polystyrene (U.S. Pat. No. 5,858,801), or a covalent reactant such as a thiol group. To create a patterned array of the bioadhesive layer, an electron-sensitive polymer such as polymethyl methacrylate (PMMA) coated onto the support can be etched in any desired pattern using an electron beam followed by development to remove the sensitized polymer. The holes in the polymer are then coated with a metal such as nickel and the polymer is removed with a solvent, leaving a pattern of metal posts on the substrate. This method of electron beam lithography provides the very high spatial resolution and small feature size required to immobilize just one molecule at each point in the patterned array. A second means for creating high-resolution patterned arrays is atomic force microscopy. A third means is X-ray lithography.

The biologics can be attached to the bioadhesive pattern by providing a polyhistidine tag on the biologic that binds to metal bioadhesive patterns. Other conventional means for attachment employ homobifunctional and heterobifunctional crosslinking reagents. Homobifunctional reagents carry two identical functional groups, whereas heterobifunctional reagents contain two dissimilar functional groups to link the biologics to the bioadhesive. A vast majority of the heterobifunctional cross-linking agents contain a primary amine-reactive group and a thiol-reactive group. Covalent crosslinking agents are selected from reagents capable of forming disulfide (S—S), glycol (—CH(OH)—CH(OH)—), azo (—N=N—), sulfone (—S(=$O_2$—), ester (—C(=O)—O—), or amide (—C(=O)—N—) bridges.

A bioresist layer may be placed or superimposed upon the bioadhesive layer either before or after attachment of the biologic to the bioadhesive layer. The bioresist layer is any material that does not bind the biologic. Examples include bovine serum albumin, gelatin, lysozyme, octoxynol, polysorbate 20 (polyethenesorbitan monolaurate) and polyethylene oxide containing block copolymers and surfactants (U.S. Pat. No. 5,858,801). Deposition of the layers is done by conventional means, including spraying, immersion and evaporative deposition (metals).

4. Labeling of NTPs

A. Attachment of a γ-Phosphate Fluorophore

The methods of the present invention involve detecting and identifying individual fluorogenic dNTP molecules as a polymerase incorporates them into a single nucleic acid molecule. In certain aspects, a fluorescent dye is attached to the γ-phosphate and a quencher is attached to the nucleobase. As such, the present invention provides a nucleotide triphosphate (NTP) probe, comprising: a NTP having a γ-phosphate with a fluorophore moiety attached thereto; a quencher moiety sufficiently proximal to the fluorophore moiety to prevent fluorescence of the fluorophore moiety; wherein the fluorophore moiety exists quenched with at least about a 5 fold quenching efficiency, preferably, at least a 10 fold quenching efficiency, when the γ-phosphate is attached to the NTP and unquenched when the γ-phosphate is detached from the NTP.

In preferred aspect, the NTP probe is a dNTP probe having a fluorescent dye attached to the γ-phosphate moiety and a quencher attached to the nucleobase. Suitable nucleobases include, but are not limited to, adenine, guanine, cytosine, uracil, thymine, deazaadenine and deazaguanosine. The quenched dNTPs are non-fluorescent when the γ-phosphate is attached to the NTP, and thereafter become fluorescent when the γ-phosphate is unattached to the NTP.

B. Fluorescence Quenching

In single molecule detection, high quenching efficiency is advantageous as it reduce fluorescence background, thus permitting the use of higher nucleotide concentrations. Several quenching mechanisms exist (see, for example, G. G. Guilbault, *Practical Fluorescence*, Marcel Dekker, New York, 1973). In certain instances, the quenching depends on spectral overlap between fluorophore and quencher, and it functions at long range (fluorescence resonance energy transfer, FRET). In other instances, the fluorophore and quencher interact between molecular orbitals and require contact between fluorophore and quencher e.g. electron transfer mechanisms. In still other instances, a ground-state complex quenching mechanism can occur. All such quenching mechanisms are within the scope of the present invention.

In certain aspects, the fluorophore moiety are fluorescent organic dyes derivatized for attachment to γ-phosphate directly or via a linker. Preferably, quencher moieties are also organic dyes, which may or may not be fluorescent, depending on the particular embodiment of the invention. For example, in one embodiment of the present invention, the fluorophore and the quencher are both fluorescent. In this embodiment, a fluorescent energy transfer mechanism can be used wherein the first fluorophore (e.g. fluorescein) is excited and emission is read from the second fluorophore (e.g. rhodamine). In these systems, dequenching is accomplished by hydrolysis of the fluorophore attached to the γ-phosphate.

In another embodiment, the fluorophore and quencher function by an electron transfer mechanism. In this aspect, a non-fluorescent quencher e.g. DABCYL or dinitrophenyl (see, FIG. 1) absorbs energy from an excited fluorophore, but does not release the energy radiatively. These quenchers can be referred to as chromogenic molecules.

There is a great deal of practical guidance available in the literature for providing an exhaustive list of fluorescent and chromogenic molecules and their relevant optical properties (see, for example, Berlman, *Handbook of Fluorescence Spectra of Aromatic Molecules*, 2nd Edition (Academic Press, New York, 1971); Griffiths, *Colour and Constitution of Organic Molecules* (Academic Press, New York, 1976); Bishop, Ed., Indicators (Pergamon Press, Oxford, 1972); Haugland, *Handbook of Fluorescent Probes and Research Chemicals* (Molecular Probes, Eugene, 1992) Pringsheim, *Fluorescence and Phosphorescence* (Interscience Publishers, New York, 1949); and the like. Further, there is extensive guidance in the literature for derivatizing fluorophore and quencher molecules for covalent attachment via common reactive groups that can be added to a nucleotide, as exemplified by the following references: Haugland (supra); Ullman et al., U.S. Pat. No. 3,996,345; Khanna et ed., U.S. Pat. No. 4,351,760.

Suitable donors and acceptors operating on the principle of fluorescence energy transfer (FET) include, but are not limited to, 4-acetamido-4'-isothiocyanatostilbene-2,2' disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5'''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144;

IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalo cyanine; and naphthalo cyanine.

Preferred fluorophore-quencher pairs include, but are not limited to, xanthene dyes, including fluoresceins, and rhodamine dyes. Many suitable forms of these compounds are widely available commercially with substituents on their phenyl moieties which can be used as the site for bonding or as the bonding functionality for attachment to the γ-phosphate or nucleobase. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Preferably, the fluorophore/quencher pair are selected from fluorescein and rhodamine dyes. These dyes and appropriate linking methodologies for attachment to nucleotides are described in many references. (see, Khanna et al. (cited above); Marshall, *Histochemical J.,* 7:299-303 (1975); Menchen et al., U.S. Pat. No. 5,188,934; Menchen et al., European Patent Application 87310256.0; and U.S. Pat. No. 5,366,860, issued to Bergot et al.).

In a preferred embodiment, the quencher 4-(4'-dimethylaminophenylazo)-benzoic acid (DABCYL) is used. The quencher DABCYL (see, FIG. 1) is commonly used in fluorogenic probes to detect DNA hybridization (molecular beacons) or protease activity. DABCYL quenches fluorescence from a wide variety of dyes emitting between 475 nm and 805 nm, with measured efficiencies ranging from 90 to 99.9% (see, S. Tyagi et al., *Nat. Biotechnol.* 16, 49 (1998); and G. T. Wang et al., *Tetrahedron Lett.* 31, 6493 (1990)). Without being bound by any particular theory, it is believed that the quenching mechanism of DABCYL probably involves electron transfer, rather than fluorescence resonance energy transfer, because it is wavelength-independent. In an equally preferred embodiment, the quenchers dinitrophenyl (DNP) or trinitrophenyl (TNP) are used.

Quenching efficiency as measured in any particular experiment depends on the purity of the dye-quencher pair (contaminating free dye or cleaved molecules fluoresce); the electronic coupling and physical distance between dye and quencher (closer is usually better); and the excited-state lifetime of the dye (the longer the time, the greater the chances for electron transfer).

In certain embodiments, certain visible and near IR dyes are known to be sufficiently fluorescent and photostable to be detected as single molecules. In this aspect the visible dye, BODIPY R6G (525/545), and a larger dye, LI-COR's near-infrared dye, IRD-38 (780/810) can be detected with single-molecule sensitivity and are used to practice the present invention.

There are many linking moieties and methodologies for attaching fluorophore or quencher moieties to nucleotides, as exemplified by the following references: Eckstein, editor, *Oligonucleotides and Analogues: A Practical Approach* (IRL Press, Oxford, 1991); Zuckerman et al., *Nucleic Acids Research,* 15: 5305-5321 (1987) (3' thiol group on oligonucleotide); Sharma et al., *Nucleic Acids Research,* 19: 3019 (1991) (3' sulfhydryl); Giusti et al., *PCR Methods and Applications,* 2: 223-227 (1993) and Fung et al., U.S. Pat. No. 4,757,141 (5' phosphoamino group via Aminolink™. II available from Applied Biosystems, Foster City, Calif.) Stabinsky, U.S. Pat. No. 4,739,044 (3' aminoalkylphosphoryl group); Agrawal et al., *Tetrahedron Letters,* 31: 1543-1546 (1990) (attachment via phosphoramidate linkages); Sproat et al., *Nucleic Acids Research,* 15: 4837 (1987) (5' mercapto group); Nelson et al., *Nucleic Acids Research,* 17: 7187-7194 (1989) (3' amino group); and the like.

Figure 2:
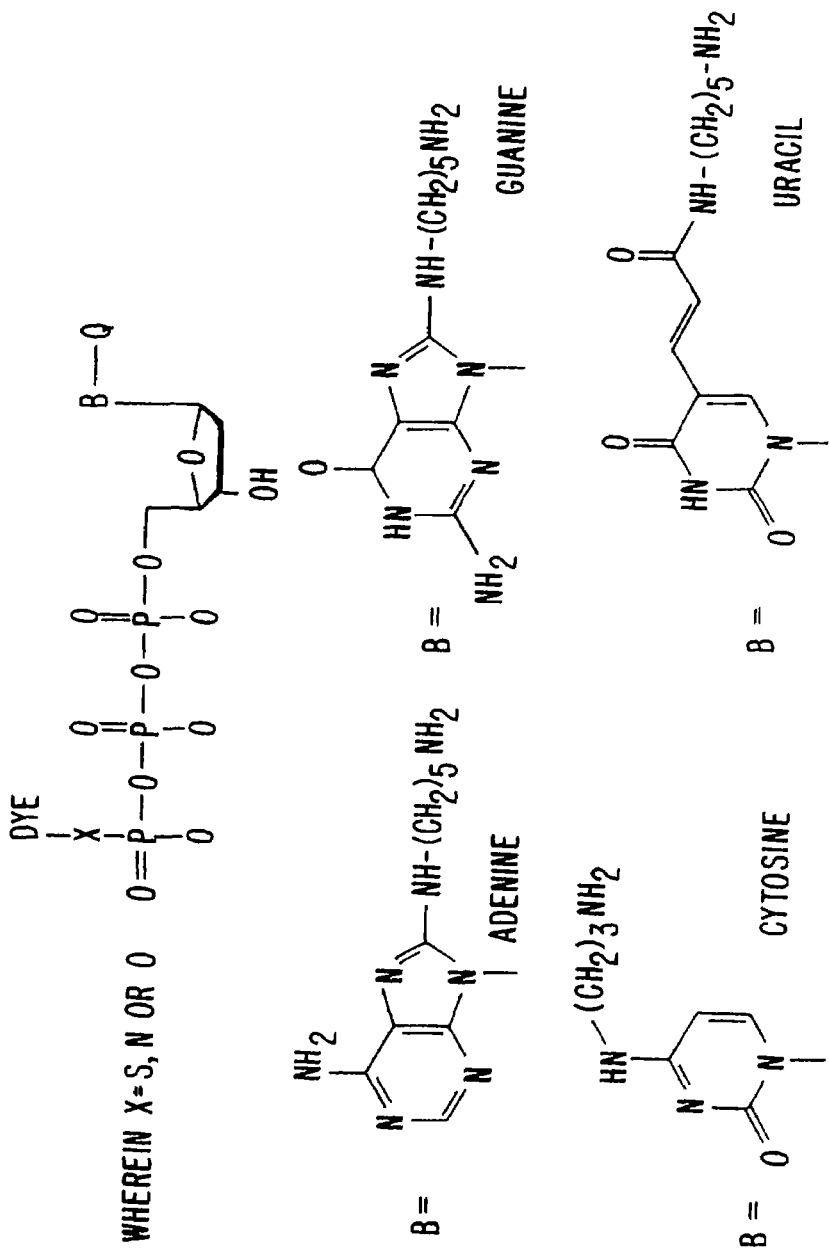
FIG. 2 describes a dye linked to the gamma phosphate of a nucleotide also bearing a quenching moiety.

With reference to FIG. 2, the preferred linkers to several bases of various dNTP structures of the present invention are shown. Again, DABCYL is a wavelength-independent fluorescence quencher having quenching efficiencies in the range required by the present methods. Better quenching permits higher dNTP concentrations and faster turnover rates. In certain aspects, the quencher is linked to the same nucleobase sites typically employed for attaching dyes (see, FIG. 1). As the polymerase progresses along the DNA, the quencher will remain at every incorporated base. In certain aspects, the quencher is covalently attached to a dNTPs using the C5 linker shown in FIG. 1. In certain embodiments, the quencher moiety is attached to the fluorophore moiety via a linker. In certain other embodiments, the quencher can be attached to the sugar of the dNTPs.

In general, nucleoside labeling can be accomplished using any of a large number of known nucleoside labeling techniques using known linkages, linking groups, and associated complementary functionalities. The linkage linking the quencher moiety and nucleoside should be compatible with relevant polymerases and not quench the fluorescence of the fluorophore moiety.

Preferably, the quenchers are covalently linked to the 5-carbon of pyrimidine bases and to the 7-carbon of 7-deazapurine bases. Several suitable base labeling procedures have been reported that can be used with the present invention, e.g. Gibson et al., *Nucleic Acids Research,* 15: 6455-6467 (1987); Gebeyehu et al., *Nucleic Acids Research,* 15: 4513-4535 (1987); Haralambidis et al., *Nucleic Acids Research,* 15: 4856-4876 (1987); Nelson et al., *Nucleosides and Nucleotides,* 5(3) 233-241 (1986); Bergstrom, et al., *JACS,* 111, 374-375 (1989); U.S. Pat. Nos. 4,855,225, 5,231, 191, and 5,449,767, each of which is incorporated herein by reference. Preferably, the linkages are acetylenic amido or alkenic amido linkages, the linkage between the quencher and the nucleotide base being formed by reacting an activated N-hydroxysuccinimide (NHS) ester of the dye with an alkynylamino- or alkenylamino-derivatized base of a nucleotide. More preferably, the resulting linkages are shown in FIG. 2.

The synthesis of alkynylamino-derivatized nucleosides is taught by Hobbs et al. in European Patent Application No. 87305844.0, and Hobbs et al., *J. Org. Chem.,* 54: 3420 (1989), which is incorporated herein by reference. As taught therein, the alkynylamino-derivatized nucleotides are formed by placing the appropriate halodeoxynucleoside (usually 5-iodopyrimidine and 7-iodo-7-deazapurine deoxynucleosides and Cu(I) in a flask, flushing with argon to remove air, adding dry DMF, followed by addition of an alkynylamine, triethyl-amine and Pd(0). The reaction mixture can be stirred for several hours, or until thin layer chromatography indicates consumption of the halodeoxynucleoside.

As taught in U.S. Pat. No. 5,047,519, which issued to Hobbs et al. on Sep. 10, 1991, the alkynylamino linkers have the structure:

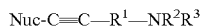

wherein $R^1$ is a substituted or unsubstituted diradical moiety of 1-20 atoms. Nuc is a purine or pyrimidine base. $R^1$ can be straight-chained alkylene, $C_1$-$C_{20}$, optionally containing within the chain double bonds, triple bonds, aryl groups or heteroatoms such as N, O or S. The heteroatoms can be part of such functional groups as ethers, thioethers, esters, amines or amides. Preferably, $R^1$ is straight-chained alkylene, $C_1$-$C_{20}$; most preferably $R^1$ is $CH_2$. Substituents on $R^1$ can include $C_1$-$C_6$ alkyl, aryl, ester, ether, amine, amide or chloro groups. $R^2$ and $R^3$ are independently H, alkyl, $C_1$-$C_4$, or a protecting group such as acyl, alkoxycarbonyl, a fluorophore, a quencher or sulfonyl. Preferably $R^2$ is H, and $R^3$ is a quencher. The alkynylamino linker is preferably attached to the 5-position of the pyrimidine nucleotides and the 7 position of the purine nucleotides.

In a preferred embodiment, a quencher-sulfoNHS derivative e.g., DABCYL-sulfoNHS is prepared using DABCYL and reacting it with N-hydroxysulfosuccinimide and N,N'-dicyclohexylcarbodiimide under a nitrogen atmosphere (see, FIG. 1). The DABCYL-sulfoNHS derivative is reacted with an aminoallyl-dNTP e.g. aminoallyl-dUTP, to produce the DABCYL-dUTP. Using the DABCYL-dUTP and cystamine dihydrochloride, a DABCYL-dUTP-thiol derivative can be generated. Thereafter, a NTP having a γ-phosphate fluorophore attached can be produced by reacting for example the DABCYL-dUTP-thiol with BODIPY TR-iodoacetamide (commercially available from Molecular Probes D-6011) to produce DABCYL-dUTP-BODIPY TR.

C. Quenching Efficiency

The present invention provides NTP molecules having a γ-phosphate with a fluorophore moiety attached thereto. The fluorophore moiety exists quenched with at least about a 5 fold quenching efficiency when the γ-phosphate is attached to the NTP and is unquenched i.e., is fluorescent, when the γ-phosphate is detached from the NTP. Preferably, the fluorophore moiety exists quenched with at least about a 3 fold quenching efficiency to about 100 fold quenching efficiency. In a more preferred embodiment, the fluorophore moiety exists quenched with at least about a 100 fold quenching efficiency to about a 1000 fold quenching efficiency.

The quenching efficiency of the NTPs of the present invention is a routine parameter easily determined. As will be apparent to those of skill in the art, quenching efficiency can be measured in a fluorometer optionally having laser excitation. Similar to the earlier discussion of the Stern-Volmer equation, quenching efficiency is equal to $$F_o-F/F_o$$

wherein $F_o$ is fluorescence of the NTP without quenching and F is the quenched fluorescence. Since there is no certain way to eliminate all fluorescence in a sample of quenched NTP, the unquenched measurements, $F_o$, can be taken in a separate sample containing dye alone and the quenched measurements, F, can be made on the same concentration of quenched dNTP.

The compounds of the present invention have at least 3 fold quenching efficiency. A fully fluorescent dye has a $F_o$ value of 1, whereas a dye quenched by 90% has an F value of 0.100. A compound quenched by 90%, has a quenching efficiency of 0.9 or is 10 fold quenched. Therefore, for compounds of the present invention, F is characterized as follows: $0.67 \leq F \leq 0.999$, i.e., the compounds possess quenching efficiencies between about 3 fold to about 1000 fold. Preferably the quenching efficiency of a compound of the present invention is about at least 5 fold to about 1000 fold, and more preferably, the quenching efficiency is about at least 10 fold to about 1000 fold.

In the present invention, detection of pyrophosphate depends on generating a fluorescent signal by dequenching, or turning on, a quenched fluorescent dye in response to pyrophosphate. Efficient quenching provides a lower background fluorescence, enhancing the signal-to-noise ratio upon dequenching by pyrophosphate. Incomplete quenching results in a low level fluorescence background from each dye molecule. Additional background fluorescence is contributed by a few of the dye molecules that are fully fluorescent because of accidental (i.e., pyrophosphate-independent) dequenching, for example by breakage of a bond connecting the dye to the quencher moiety. Thus, the background fluorescence has two components: a low-level fluorescence from all dye molecules, referred to herein as "distributed fluorescence background" and full-strength fluorescence from a few molecules, referred to herein as "localized fluorescence background".

In instances where a multi-labeling scheme is utilized, a wavelength which approximates the mean of the various candidate labels' absorption maxima may be used. Alternatively, multiple excitations may be performed, each using a wavelength corresponding to the absorption maximum of a specific label. Table I lists examples of various types of fluorophores and their corresponding absorption maxima.

TABLE I

| Candidate Fluorophores | Absorbance/Emission |
| --- | --- |
| Rho123 | 507/529 |
| R6G | 528/551 |
| BODIPY 576/589 | 576/589 |
| BODIPY TR | 588/616 |
| Nile Blue | 627/660 |
| BODIPY 650/665 | 650/665 |
| Sulfo-IRD700 | 680/705 |
| NN382 | 778/806 |
| Tetramethylrhodamine | 550 |
| Rodamine X | 575 |
| Cy3 TM | 550 |
| Cy5 TM | 650 |
| Cy7 TM | 750 |

5. Miscellaneous Reaction Reagents

The polymerase selected for use in this invention is not critical. Preferred polymerases are able to tolerate labels both on the nucleobase and on the gamma-phosphate. The polymerase should have a fidelity (incorporation accuracy) of at least 99% and a processivity (number of nucleotides incorporated before the enzyme dissociates from the DNA) of at least 20 nucleotides, with greater processivity preferred. Examples include T7 DNA polymerase, T5 DNA polymerase, HIV reverse transcriptase, E. coli DNA pol I, T4 DNA polymerase, T7 RNA polymerase, Taq DNA polymerase and E. coli RNA polymerase. Exonuclease-defective versions of these polymerases are preferred.

The primers (DNA polymerase) or promoters (RNA polymerase) are synthetically made using conventional nucleic acid synthesis technology. The complementary strands of the probes are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, *Tetrahedron*, 48: 2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the polymerase. They can be ordered commercially from a variety of companies which specialize in custom oligonucleotides such as a Operon Inc. (Alameda, Calif.).

Primers in combination with polymerases are used to sequence target DNA. Primer length is selected to provide for hybridization to complementary template DNA The primers will generally be at least 10 by in length, usually at least between 15 and 30 bp in length. Primers are designed to hybridize to known internal sites on the subject target DNA. Alternatively, the primers can bind to synthetic oligonucleotide adaptors joined to the ends of target DNA by a ligase. Similarly where promoters are used, they can be internal to the target DNA or ligated as adaptors to the ends.

6. Reaction Conditions

The reaction mixture for the sequencing comprises an aqueous buffer medium which is optimized for the particular polymerase. In general, the buffer includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000 micromhos.

The divalent cation may be magnesium, managanese, zinc and the like, where the cation will typically be magnesium. Any convenient source of magnesium cation may be employed, including $MgCl_2$, Mg-acetate, and the like. The amount of Mg ion present in the buffer may range from 0.5 to 20 mM, but will preferably range from about 1 to 12 mM, more preferably from 2 to 10 mM and will ideally be about 5 mM.

Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.6 at 25° C. Other agents which may be present in the buffer medium include chelating agents, such as EDTA, EGTA and the like.

7. Sample Housing

The solid support is optionally housed in a flow chamber having an inlet and outlet to allow for renewal of reactants which flow past the immobilized moieties. The flow chamber can be made of plastic or glass and should either be open or transparent in the plane viewed by the microscope or optical reader. Electro-osmotic flow requires a fixed charge on the solid support and a voltage gradient (current) passing between two electrodes placed at opposing ends of the solid support. The flow chamber can be divided into multiple channels for separate sequencing. Examples of micro flow chambers exist. For example, Fu et al. (*Nat. Biotechnol.* (1999) 17:1109) describe a microfabricated fluorescense-activated cell sorter with 3 μm×4 μm channels that utilizes electro-osmotic flow for sorting.

8. Detection of Fluorophores

This invention requires the imaging of single molecules in a solution. There are a variety of known ways of achieving this goal. General reviews are available describing this technology. Reviews include Basche et. al., eds., 1996, Single molecule optical detection, imaging, and spectroscopy, Weinheim:VCM, and Plakhotnik, et. al., Single-molecule spectroscopy, *Ann. Rev. Phys, Chem.* 48: 181-212. In general, the methods involve detection of laser activated fluorescence using microscope equipped with a camera. It is sometimes referred to as a high-efficiency photon detection system. Nie, et. al., 1994, Probing individual molecules with confocal fluorescence microscopy, *Science* 266:1018-1019. The detection of single molecules involves limiting the detection to a field of view in which one has a statistical reason to believe there is only one molecule (homogeneous assays) or to a field of view in which there is only one actual point of attachment (heterogeneous assays). The single-molecule fluorescence detection of the present invention can be practiced using optical setups including near-field scanning microscopy, far-field confocal microscopy, wide-field epi-illumination, and total internal reflection fluorescence (TIRF) microscopy. For two-dimensional imaging fluorescence detection, the microscope is typically a total internal reflectance microscope. Vale et. al., 1996, Direct observation of single kinesin molecules moving along microtubules, *Nature* 380: 451, Xu and Yeung 1997, Direct Measurement of Single-Molecule Diffusion and Photodecomposition in Free Solution, *Science* 275: 1106-1109.

Suitable photon detectors include, but are not limited to, photodiodes and intensified CCD cameras. In a preferred embodiment, an intensified charge couple device (ICCD) camera is used. The use of a ICCD camera to image individual fluorescent dye molecules in a fluid near the surface of the glass slide is advantageous for several reasons. With an ICCD optical setup, it is possible to acquire a sequence of images (movies) of fluorophores. In certain aspects, each of the NTPs of the present invention has a unique fluorophore associated with it, as such, a four-color instrument can be used having four cameras and four exitation lasers. Thus, it is possible to use this optical setup to sequence DNA. In addition, many different DNA molecules spread on a microscope slide can be imaged and sequenced simultaneously. Moreover, with the use of image analysis algorithms, it is possible to track the path of single dyes and distinguish them from fixed background fluorescence and from "accidentally dequenched" dyes moving into the field of view from an origin upstream.

In certain aspects, the preferred geometry for ICCD detection of single-molecules is total internal reflectance fluorescence (TIRF) microscopy. In TIRF, a laser beam totally reflects at a glass-water interface. The optical field does not end abruptly at the reflective interface, but its intensity falls off exponentially with distance. The thin "evanescent" optical field at the interface provides low background and enables the detection of single molecules with signal-to-noise ratios of 12:1 at visible wavelengths (see, M. Tokunaga et al., *Bio-* chem. and Biophys. Res. Comm. 235, 47 (1997) and P. Ambrose, *Cytometry*, 36, 244 (1999)).

The penetration of the field beyond the glass depends on the wavelength and the laser beam angle of incidence. Deeper penetrance is obtained for longer wavelengths and for smaller angles to the surface normal within the limit of a critical angle. In typical assays, fluorophores are detected within about 200 nm from the surface which corresponds to the contour length of about 600 base pairs of DNA. Preferably, a prism-type TIRF geometry for single-molecule imaging as described by Xu and Yeung is used (see, X-H. N. Xu et al., *Science*, 281, 1650 (1998)).

Single molecule detection can be achieved using flow cytometry where flowing samples are passed through a focused laser with a spatial filter used to define a small volume. U.S. Pat. No. 4,979,824 describes a device for this purpose. U.S. Pat. No. 4,793,705 describes and claims in detail a detection system for identifying individual molecules in a flow train of the particles in a flow cell. The '705 patent further describes methods of arranging a plurality of lasers, filters and detectors for detecting different fluorescent nucleic acid base-specific labels. U.S. Pat. No. 4,962,037 also describes a method for detecting an ordered train of labeled nucleotides for obtaining DNA and RNA sequences using a nuclease to cleave the bases rather than a polymerase to synthesize as described herein. Single molecule detection on solid supports is described in Ishikawa, et al. (1994) Single-molecule detection by laser-induced fluorescence technique with a position-sensitive photon-counting apparatus, *Jan. J. Apple. Phys.* 33:1571-1576. Ishikawa describes a typical apparatus involving a photon-counting camera system attached to a fluorescence microscope. Lee et al. (1994), Laser-induced fluorescence detection of a single molecule in a capillary, *Anal. Chem.*, 66:4142-4149 describes an apparatus for detecting single molecules in a quartz capillary tube. The selection of lasers is dependent on the label and the quality of light required. Diode, helium neon, argon ion, argon-krypton mixed ion, and Nd:YAG lasers are useful in this invention.

Figure 4:
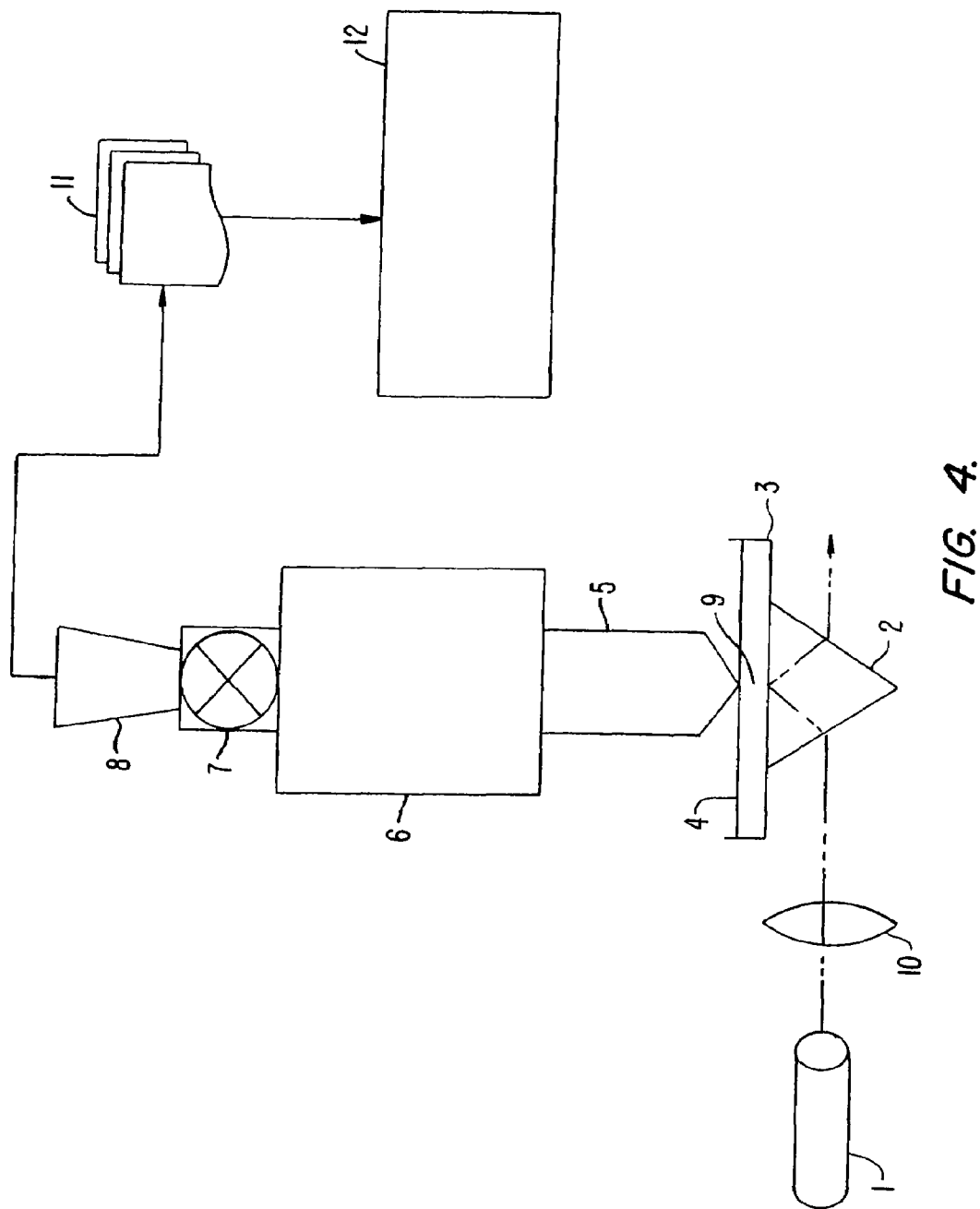
FIG. 4 is an overview of the system for polymerase synthesis sequencing of target nucleic acid.
Figure 5:
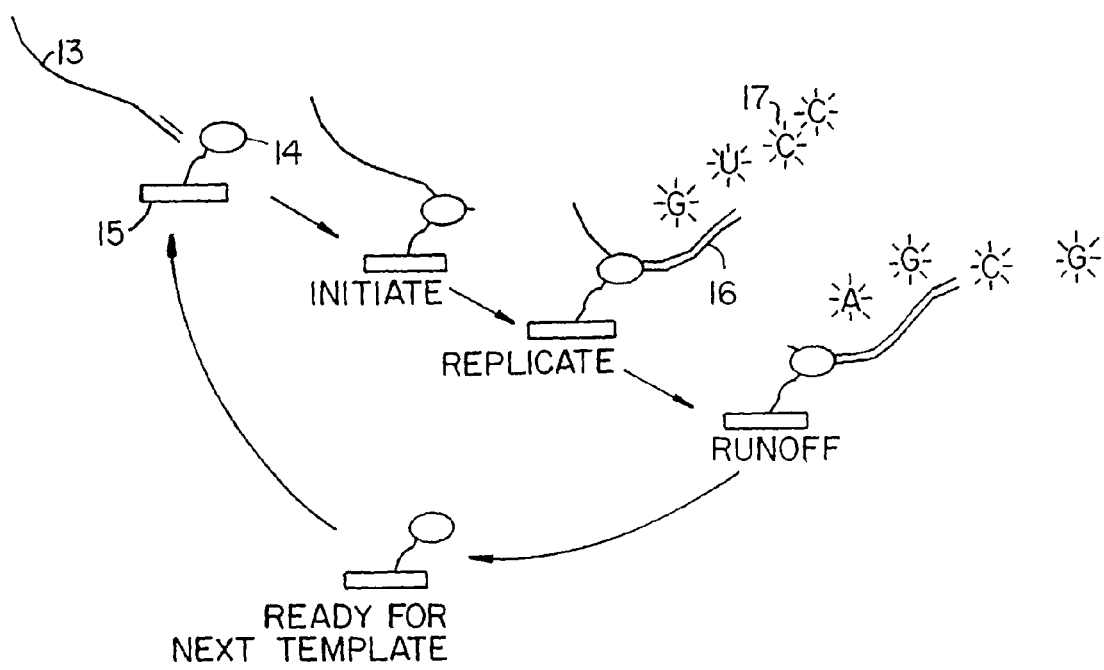
FIG. 5 is a schematic view of the method where a DNA polymerase is immobilized onto a solid support and the target nucleic acid is DNA.

This invention can be viewed as a system of components designed to detect the synthesis of a nucleic acid as PPi is released. FIG. 4 provides an overview of this system which is described in detail in Example 2. FIG. 5 illustrates a typical arrangement of the polymerase (14) immobilized on the surface of the solid support (15) with a target DNA (13) being extended by the incorporation of gamma labeled dNTPs (17). More specifically, the target DNA is hybridized to a primer that will become the extension product generated by the tethered DNA dependent DNA polymerase.

Figure 6:
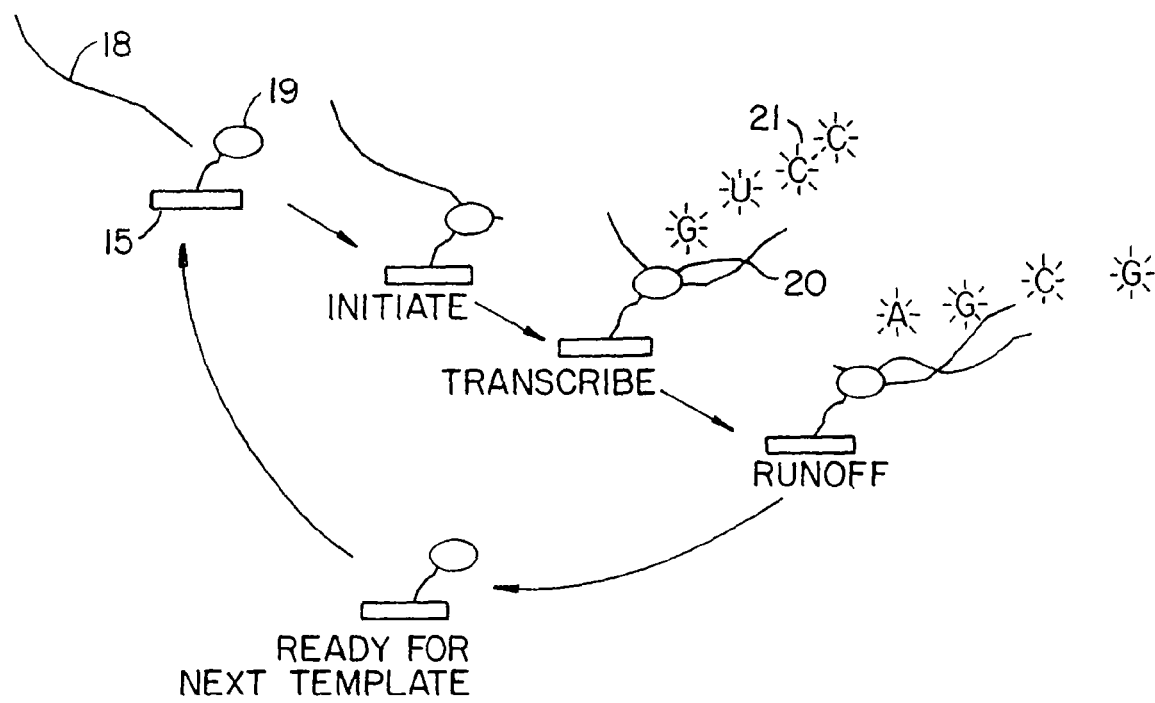
FIG. 6 is a schematic view of the method where a RNA polymerase is immobilized onto a solid support and the target nucleic acid is double stranded DNA.

FIG. 6 illustrates a continuous sequences of double stranded DNA molecules (18) using double stranded DNA dependent RNA polymerase (19) immobilized on a solid support (15) where the extension product is transcribed as a new RNA (20) from the labelled rNTPs (21). More specifically, a double stranded DNA template binds to the RNA polymerase through sequence recognition of a polymerase promoter sequence. The sequence is read as the DNA travels through the enzyme yielding a nascent RNA. After the RNA and DNA are released, the enzyme is ready to sequence the next DNA molecule passing by.

These schemes ensure that the active site remains in the evanescent light field at the surface, so that every dye released from a quenched dNTP is illuminated. Tethering of the polymerase, rather than the target nucleic acid (template) is convenient because it provides for a continuous sequencing process where one immobilized enzyme sequences many different DNA molecules.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1

Polymerase Array

This example shows how to fabricate an array of nickel nanodots and attach a polymerase to each dot. The required equipment includes a spinner (PWM 202 E-beam resist spinner, Headway Research Inc.), an evaporator (SC4500 thermal e-gun evaporator, CVC Products Inc.), and a scanning electron microscope (Leo 982 with Nabity pattern generator, Leo Electron Microscopy Inc.).

Clean a 25 mm diameter microscope coverslip on the spinner by spraying alternately with acetone and isopropyl alcohol (IPA) and spinning the last IPA film until dry. Coat the coverslip in the spinner with 0.5 ml of PMMA (poly(methyl methylacrylate), MW 496 kDa, 2% in chlorobenzene), bake on a hoplate at 170 C for 10 min, coat with 0.5 ml of PMMA (MW 950 kDa, 2% in methyl isobutyl ketone [MIBK]), and bake again. Apply the conductive layer by evaporating 100 Angstroms of gold onto the PMMA film in the CVC SC4500. Use the electron microscope to etch the array pattern into the PMMA film using a pattern generator on the Leo 982 as specified by a CAD drawing (Design CAD, 50 nm spots, 10 µm center-to-center spacing, 200×200 dot array).

Remove the gold layer by placing the exposed coverslip in Gold Etch (15-17% sodium iodide) for 7 seconds followed by rinsing with IPA and water. Deposit Tantalum (50 Angstroms) and Nickel (100 Angstroms) on the coverslip in the CVC SC4500. Remove the PMMA in a 1:1 mix of acetone and methylene chloride for 10-15 min followed by sonication for several seconds and rinsing with IPA and water.

Attach the polymerase just before use by applying 10 ul of a 15 nM solution of polyhistidine-tagged Klenow DNA polymerase ex$^-$ (prepared using TOPO cloning vector and Pro-Bond Resin, Invitrogen Inc.) in phosphate-buffered saline (PBS; Harlow E., Lane D. 1988. Antibodies A Laboratory Manual. Cold Spring Harbor Laboratory ISBN 0-87969-14-2) to the coverslip; after 20 min, wash the coverslip in PBS and use immediately.

Example 2

Two-Color Single-Molecule Imaging Microscope

The microscope described in FIG. 4 is used to detect single molecule events on the surface of the coverslip obtained in Example 1. The microscope is fitted with a multicolor mixed-gas laser (1) which emits light at tunable wavelengths. The laser beam is first passed through a laser line filter (10) in order to filter out undesirable wavelengths. The unfocused output passes to a fused-silica right angle prism (2), which is located directly under the cover slip (3). The sample (4) molecules sit in a buffer solution on the cover slip.

Laser light entering the prism is refracted at an angle such that the critical angle between fused-silica and the buffer solution is exceeded. The light is thus completely reflected within the prism, giving rise to a total internal reflection (TIR) evanescent field (9) in the buffer. The area of interest is imaged using a microscope (6) with an objective lens (5) immersed directly in the buffer. Fluorescence emission at the microscope output passes through a multi-wavelength viewer (7), which spatially separates images at different wavelengths. This allows the discrimination of events occurring at different wavelengths.

The images are projected onto the array of an intensified CCD (ICCD) camera (8), from which they are digitized and stored in memory (11). Image analysis algorithms (12) are performed on the images stored in memory. These algorithms may distinguish signal from background, track molecules, and perform other signal processing functions. The memory and signal processing may be performed off-line in a computer, or in specialized digital signal processing (DSP) chips controlled by a microprocessor.

Example 3

Synthesis of Dual-Labeled Nucleotides

Example 3A

Figure 3:
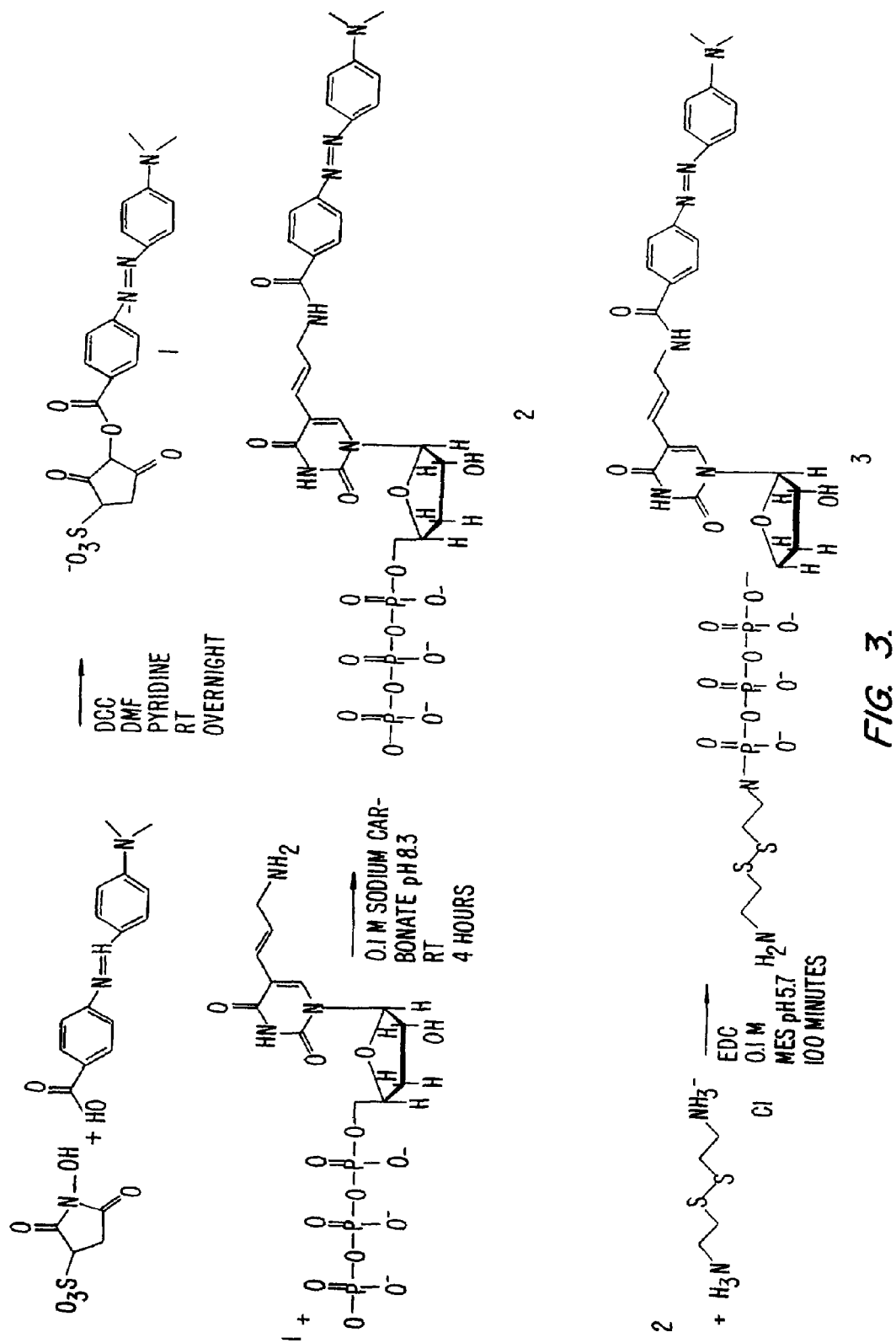
FIG. 3 is an overview of a synthetic pathway for generating nucleotides with fluorophores on the gamma phosphate and the quenching moiety on the base.
Figure 3:
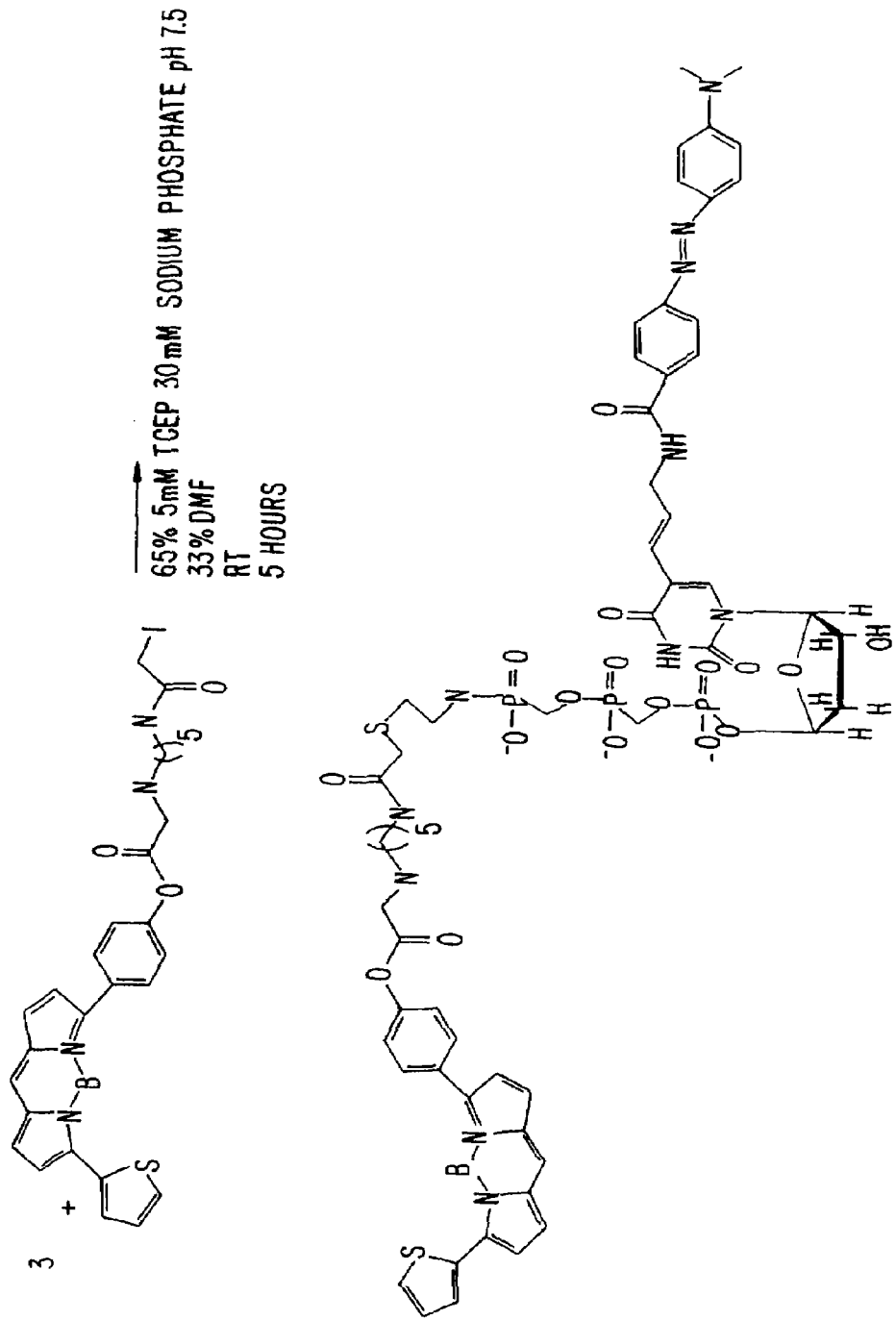

The Synthesis of DABCYL-dUTP-BODIPY TR. (FIG. 3)

a. Preparation of DABCYL-sulfoNHS

DABCYL (108 mg, 0.4 mmole; Aldrich 25,019-8 Methyl red) was dissolved in a mixture of dry N,N-dimethylformamide (10 mL; Aldrich 22,705-6) and dry pyridine (96 mg, 1.2 mmole; Aldrich 27,097-0). N-Hydroxysulfosuccinimide (260 mg, 1.2 mmole; Pierce 24510) and N,N'-dicyclohexylcarbodiimide (250 mg, 1.2 mmole; Pierce 20320) were added and the mixture was stirred at 50° C. for 2 hours under a nitrogen atmosphere. The reaction was monitored by TLC (MKC18F Reversed Phase; Whatman 4803-110; developed in 0.1 M triethylammonium acetate, pH 7, 80% acetonitrile). After dilution with ether, the supernatant was decanted, the product was washed with ether on a filter, dried, and stored dessicated at −20° C.

b. Synthesis of DABCYL-dUTP

Aminoallyl-dUTP (10 mg, 20 μmole; Sigma A 0410) was mixed with DABCYL-sulfoNHS (30 mg, 30 μmole; from step A) in 3 mL of 0.1 M sodium carbonate pH 8.3. The mixture was incubated in the dark for 4 hours at room temperature and the reaction was monitored by TLC (as in step A). The DABCYL-dUTP product was purified by reversed-phase HPLC using a linear gradient from 0% to 100% of Buffer B mixed into Buffer A over 20 minutes (Buffer A is 0.1 M triethylammonium acetate in water, pH 7, 4% acetonitrile; Buffer B is the same as Buffer A with 80% acetonitrile).

c. Synthesis of DABCYL-dUTP-thiol

DABCYL-dUTP (9 mg, 12 mmole; from step B) was dissolved in 1 mL of 0.1 M MES pH 5.7 (Sigma M 3023) and adjusted to pH 5.75. Cystamine dihydrochloride (10 mg, 44 μmol; Sigma C 8707) was dissolved in 2.5 mL of 0.1 M MES pH 5.7 and adjusted to pH 5.75. EDC (9 mg, 47 μmol; Pierce 22980) was dissolved in 0.5 mL of 0.1 M MES pH 5.7 and was added immediately to the DABCYL-dUTP solution. After 10 minutes, the cystamine solution was added and the pH was maintained between 5.5 and 5.8 while the reaction proceeded at room temperature. After two hours, the pH was adjusted to 7.0 and the sample was stored at −20° C. The product was purified by reversed-phase HPLC as in step b.

d. Synthesis of DABCYL-dUTP-BODIPY TR

DABCYL-dUTP-thiol (2.5 mg, 3 mole; from step C) was dissolved in 5.4 mL of 5 mM TCEP (Pierce 20490), 30 mM sodium phosphate adjusted to pH 7.5. BODIPY TR-iodoacetamide (5 mg, 7.4 umol; Molecular Probes D-6011) was dissolved in 2.6 mL of N,N-dimethylformamide and was added to the DABCYL-dUTP-thiol solution. After standing at room temperature in the dark for 5 hours, the product was purified by reversed-phase HPLC as in step b.

e. Determination of Quenching Efficiency

The quenching efficiency of DABCYL-dUTP-BODIPY TR was determined as follows. First, the fluorescence of a sample containing the dye BODIPY TR is measured. Second, a sample containing the same concentration of the nucleotide triphosphate having a γ-phosphate with a fluorophore moiety attached i.e., DABCYL-dUTP-BODIPY TR is measured. Thereafter, the quenching efficiency, which is equal to $F_o-F/F_o$ wherein $F_o$ is fluorescence of the BODIPY TR alone and F is the fluorescence of DABCYL-dUTP-BODIPY TR is calculated. The fluorescence quenching efficiency of DABCYL-dUTP-BODIPY TR is at least 5 fold compared to the BODIPY TR alone.

Example 3B

Synthesis of Rho-dUTP-BODIPY TR and Rho-dCTP-BODIPY TR a. Synthesis of Rho-dUTP

Aminoallyl-dUTP (20 umole; Sigma A 0410) was mixed with 5-carboxyrhodamine 6G, succinimidyl ester (30 umole; Molecular Probes C-6127) in 3 ml of 0.1 M sodium carbonate pH 8.3, 20% DMF. The mixture was incubated in the dark at room temperature and the reaction was monitored by TLC (MKC18F Reversed Phase; Whatman 4803-110; developed in 0.1 M triethylammonium acetate, pH 7, 80% acetonitrile). The Rho-dUTP product was purified by reversed-phase HPLC using a linear gradient from 0% to 100% of Buffer B mixed into Buffer A over 20 minutes (Buffer A is 0.1 M triethylammonium acetate in water, pH 7, 4% acetonitrile; Buffer B is the same as Buffer A with 80% acetonitrile).

b. Synthesis of Rho-dUTP-thiol

Rho-dUTP (12 umole; from step a) was dissolved in 1 ml of 0.1 M MES pH 5.7 (Sigma M 3023) and adjusted to pH 5.75. Cystamine dihydrochloride (44 mmol; Sigma C 8707) was dissolved in 2.5 ml of 0.1 M MES pH 5.7 and adjusted to pH 5.75. EDC (47 umol; Pierce 22980) was dissolved in 0.5 ml of 0.1 M MES pH 5.7 and was added immediately to the Rho-dUTP solution. After 10 minutes, the cystamine solution was added and the pH was maintained between 5.5 and 5.8 while the reaction proceeded at room temperature. After two hours, the pH was adjusted to 7.0 and the sample was stored at −20 C. The product was purified by reversed-phase HPLC as described in step a.

c. Synthesis of Rho-dUTP-BODIPY TR

Rho-dUTP-thiol (3 umole; from step b) was dissolved in 5.4 ml of 5 mM TCEP (Pierce 20490), 30 mM sodium phosphate adjusted to pH 7.5. BODIPY TR-iodoacetamide (7.4 umol; Molecular Probes D-6011) was dissolved in 2.6 ml of N,N-dimethylformamide and was added to the Rho-dUTPthiol solution. After standing at room temperature in the dark for 5 hours, the product was purified by reversed-phase HPLC as in step a.

d. Synthesis of Rho-dCTP-BODIPY TR

Labeled dCTP was made essentially as described for dUTP, except that aminoallyl-dCTP was substituted for the dUTP. Aminoallyl-dCTP was synthesized according to U.S. Pat. No. 5,476,928 except that dCTP was used instead of dUTP.

Example 4

Genotyping

This example illustrates a sequence-based genotyping assay on single DNA molecules. The target is the (Delta)F508 deletion of the cystic fibrosis transmembrane conductance regulator gene (Welsh M J, et al., 1993. *J Cell Science* 106S: 235-239). Genomic DNA is isolated from whole blood of CFTR-homozygous individuals (Wizard Genomic DNA Purification Kit Cat. No. A1120, Promega Inc.). Amplify a 54-nucleotide segment of the CFTR gene by PCR using the primers 5' CACCATTAAAGAAAATATCAT (primer 1; SEQ ID NO:1) and 5'-Biotinyl-CTGTATCTATATTCATCATAG (primer 2; SEQ ID NO:2).

The custom primers are obtained from a commercial source (e.g., Operon Technologies, Alameda, Calif.). Primer 1 hybridizes to the CFTR sequence adjacent to the (Delta) F508 deletion; the first nucleotide 3' to primer 1 is cytosine in the normal allele or thymine in the deletion mutant (see Table 2 below; from Vaughan P, McCarthy T. 1998. *Nuc Acids Res* 26: 810-815). Amplification conditions are 200 ng of genomic DNA, 0.2 mM each of dATP, dCTP, dGTP and dUTP, 0.2 uM of each primer, 2.0 mM MgCl2, 1 unit of Taq DNA polymerase, 50 mM KCl, 10 mM Tris-HCl (pH 9 at 25 C), 0.1% Triton X-100, in a final volume of 50 ul (30 cycles of 94 C for 30 sec, 52 C for 30 sec, 72 C for 15 sec; optimization of Mg concentration and cycling parameters may be necessary, depending on the particular characteristics of the thermal cycler device employed).

Purify the PCR product on streptavidin-coated magnetic beads (DYNAPURE Dye Terminator Removal kit, Dynal A.S.) and re-amplify for 15 cycles under the same conditions as before, except replace the genomic DNA with 2 ul of the purified amplification product and omit primer 1 in order to produce an excess of the single-stranded DNA product complementary to primer 1. Remove the dNTPs from the amplified product ("template-primer") using magnetic beads as before.

Place 10 µl of reaction mix (30 nM template-primer, 100 nM primer 1, 1 nM Rho-dCTP-BTR (Example 3), 10 mM Tris-HCl (pH 7.5), 5 mM MgCl₂, 7.5 mM dithiothreitol) onto the polymerase array on the two-color single-molecule imaging microscope of Example 2 and acquire a series of images for 20 minutes. Similarly analyze a second sample that is identical to the first except that Rho-dCTP-BTR of the first sample is replaced with Rho-dUTP-BTR (Example 3). Analyze the image sets for incorporation events as indicated by separation of the two coupled dyes from one another. Compare the number of events observed using dCTP (sample 1) and dUTP (sample 2) to determine whether the test CFTR gene is the normal or deletion allele.

TABLE 2

Normal Allele
(SEQ ID NO: 3)
CACCATTAAAGAAAATATCATCTTTGGTGTTTCCTATGATGAATATAGAT
ACAG
GTGGTAATTTCTTTTATAGTAGAAACCACAAAGGATACTACTTATATCTA
TGTC Deletion Mutant
(SEQ ID NO: 4)
CACCATTAAAGAAAATATCATTGGTGTTTCCTATGATGAATATAGATACA
G
GTGGTAATTTCTTTTATAGTAACCACAAAGGATACTACTTATATCTATG
TC The primers are underlined (primer 1 at left, primer 2 at right). The three deleted base pairs are indicated in bold type in the normal sequence.

Example 5

Sequencing

Sequencing is accomplished as for genotyping (Example 4), with reading of more than one nucleotide downstream of the primer.

a) Synthesis of BODIPY TR-dUTP-Rhodamine

Follow the procedure of Example 3a to make BODIPY TR-dUTP, substituting BODIPY TR-X STP ester (Molecular Probes B-10003) for the rhodamine of Example 3a. Derivatize the BODIPY TR-dUTP with a thiol as in Example 3b, and conjugate tetramethylrhodamine-5-iodoacetamide dihydroiodide (Molecular Probes T-6006) to the thiol as in Example 3c.

b) Sequencing

Use the same normal allele DNA template as prepared in Example 4. Place 10 ul of reaction mix (30 nM template-primer, 100 nM primer 1, 1 nM BODIPY TR-dUTP-Rho (Example 5a), 1 nM Rho-dCTP-BODIPY TR (Example 3d), 10 mM Tris-HCl (pH 7.5), 5 mM MgCl₂, 7.5 mM dithiothreitol) onto the polymerase array on the two-color single-molecule imaging microscope of Example 2 and acquire an image series. Incorporation of dUTP is seen by separation of the two dyes, with the rhodamine being released. Incorporation of dCTP is detected by separation of the same two dyes, but with the Rhodamine being released instead of the BODIPY.

What is claimed is:

1. A method for sequencing a target nucleic acid molecule in a system having a flow chamber with a support, said method comprising:
   (a) providing a flow chamber with a support comprising an array of immobilized complexes, each of said immobilized complexes comprising a nucleic acid polymerizing enzyme, a target nucleic acid, and a primer which complements a region of the target nucleic acid, wherein the nucleic acid polymerizing enzyme is complexed with the target nucleic acid and the primer, and either the nucleic acid polymerizing enzyme or the target nucleic acid is immobilized on the support;
   (b) introducing into the chamber a plurality of nucleotide analogs with labels on their γ-phosphates that are not positioned on said support to move through said flow chamber to contact said complexes;
   (c) extending the primer by incorporating nucleotide analogs from the plurality of nucleotide analogs into the primer, thereby forming a polymerase extension product, which is a complement of the target nucleic acid; and
   (d) sequencing the target nucleic acid by individually detecting the labels of the γ-phosphates from the nucleotide analogs during a process in which the polymerase extension product is formed.

2. The method of claim 1, wherein said labels are attached to the γ-phosphates via a linker.

3. The method of claim 1, wherein said labels are directly attached to the γ-phosphates.

4. The method of claim 1, wherein said flow chamber is made of plastic or glass.

5. The method of claim 1, wherein said individually detecting the labels of the γ-phosphates from the nucleotide analogs is performed using a detector which is capable of detecting a single molecule.

6. The method of claim 5, wherein said detector is selected from the group consisting of an optical reader, a high-efficiency photon detection system, a photodiode, a camera, a charge couple device, an intensified charge coupled device, a near-field scanning microscope, a far-field confocal microscope, a microscope that detects wide-field epi-illumination, and a total internal reflection fluorescence microscope when the labels are fluorescent labels.

7. The method of claim 1, wherein the nucleic acid polymerizing enzyme or the target nucleic acid is present as an individual molecule located in a defined location of the support.

8. The method of claim 1, wherein each of the immobilized complexes of said array is different.

9. The method of claim 1, wherein said array of immobilized complexes is addressable.

10. The method of claim 5, wherein said detector is capable of acquiring a sequence of images.

11. The method of claim 10, wherein said sequence of images is analyzed to track single molecules.

12. The method of claim 5, wherein said detector provides low background and enables the detection of single molecules.

13. The method of claim 5, wherein said detector detects the labels in an evanescent optical field when the labels are fluorescent labels.

14. The method of claim 5, wherein said detector detects the labels via a mechanism selected from the group consisting of fluorescence resonance energy transfer, an electron transfer mechanism, an excited-state lifetime mechanism and a ground-state complex quenching mechanism when the labels are fluorescent labels.

* * * * *